US00PP33290P2

(12) United States Plant Patent
Wood

(10) Patent No.: US PP33,290 P2
(45) Date of Patent: Jul. 27, 2021

(54) ***HYDRANGEA* PLANT NAMED 'SMNHRLL'**

(50) Latin Name: ***Hydrangea arborescens* subsp. *radiata***
Varietal Denomination: SMNHRLL

(71) Applicant: Spring Meadow Nursery, Inc., Grand Haven, MI (US)

(72) Inventor: Timothy D Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/115,110

(22) Filed: Dec. 8, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHRLL' is disclosed, characterized by large white and light pink flowers arranged in a lacecap inflorescence on plants with strong stems. The new variety is a *Hydrangea*, normally produced as an ornamental plant.

2 Drawing Sheets

Latin name of the genus and species: *Hydrangea arborescens* subsp. *radiata.*

Variety denomination: 'SMNHRLL'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with good plant habit and showy flowers. The open-pollination resulting in this new variety was made during the summer 2011.

The parent varieties cannot be identified as this new selection resulted from an open-pollination in which seed was bulk collected from various seed parents.

The new variety was identified as a potentially interesting selection in the Summer of 2016, at a commercial greenhouse in Grand Haven, Mich.

Asexual reproduction of the new cultivar 'SMNHRLL' by vegetative softwood cuttings was first performed during the Summer of 2015, at a commercial greenhouse in Grand Haven, Mich. Subsequent asexual propagation has shown that the unique features of this cultivar are stable and reproduced true to type in four successive generations.

SUMMARY OF THE INVENTION

The cultivar 'SMNHRLL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHRLL' These characteristics in combination distinguish 'SMNHRLL' as a new and distinct *Hydrangea* cultivar:

1. Large flowers.
2. Attractive white and light pink flowers arranged in a lacecap inflorescence.
3. Strong stems.

PARENT COMPARISONS

The parent varieties cannot be accurately identified for comparison.

COMMERCIAL COMPARISON

Plants of the new cultivar 'SMNHRLL' can be compared to the variety *Hydrangea* 'Haas Halo', U.S. Plant Pat. No. 24,783. These varieties are similar in most horticultural characteristics, however 'SMNHRLL' differs in the following:

1. The new variety has pink fertile flowers; this comparator as green-white fertile flowers
2. This new variety has red stems; this comparator has green stems.
3. The new variety has a more upright plant habit than this comparator.
4. Sepals on the sterile flowers of the new variety are light pink; sepals on the sterile flowers of this comparator are white to green.

Plants of the new cultivar 'SMNHRLL' can be compared to the variety *Hydrangea* 'Dardorn', U.S. Plant Pat. No. 14,168. These varieties are similar in most horticultural characteristics, however 'SMNHRLL' differs in the following:

1. The new variety has pink fertile flowers; this comparator as green-white fertile flowers
2. This new variety has red stems; this comparator has green stems.
3. The new variety has larger flowers and a smaller quantity of flowers, this comparator has smaller flowers, in larger quantity.

4. Foliage of the new variety is thicker and more leathery than foliage of this comparator.

BRIEF DESCRIPTION OF THE PHOTOGRAPHS

'SMNHRLL' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new *Hydrangea*.

DETAILED BOTANICAL DESCRIPTION

Figure 1:
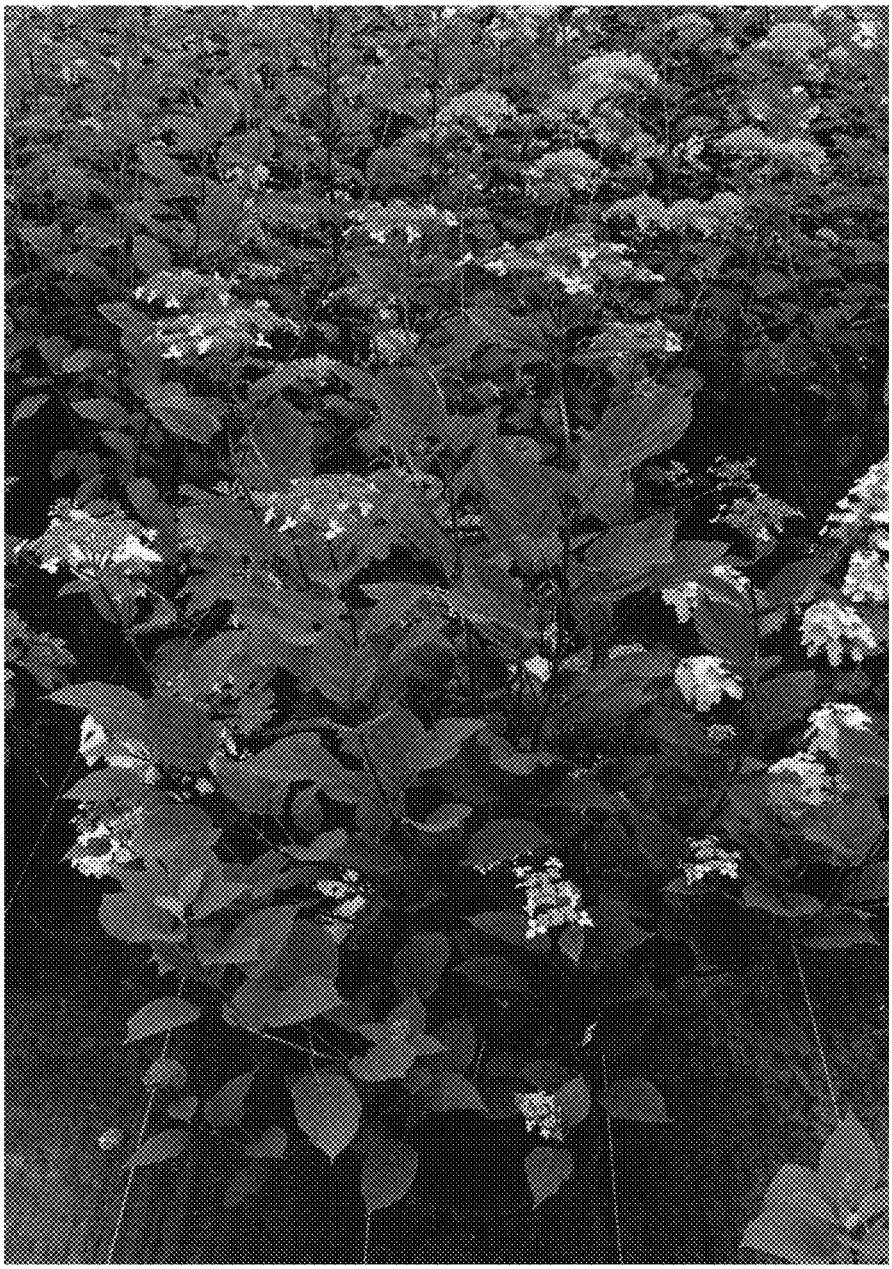
FIG. 1 shows a flowering plant of 'SMNHRLL' grown in Grand Haven, Mich. at the age of approximately 18 months grown in a poly house.
Figure 2:
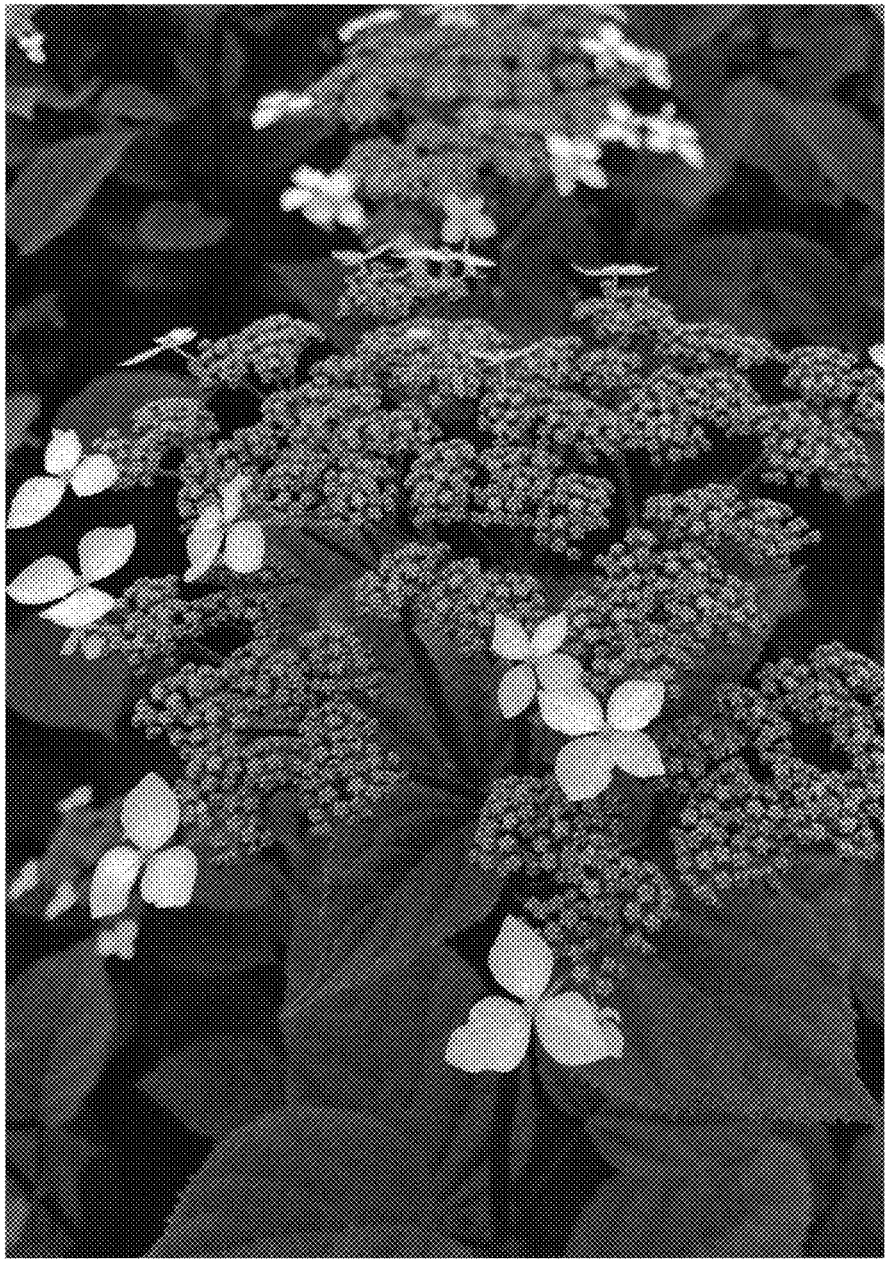
FIG. 2 shows a close-up view of the mature inflorescence during Summer.

In the following description, color references are made to The Royal Horticultural Society Color Chart 2015 except where general terms of ordinary dictionary significance are used. The following observations and measurements describe 'SMNHRLL' plants grown in a commercial poly greenhouse in Grand Haven, Mich. under natural lighting. Measurements were taken during Summer and Fall of 2020. The plants were about 2 to 3 years old planted in the ground. The growing temperature ranged from 5° C. to 27° C. Measurements and numerical values represent averages of typical plant types.

Botanical classification: *Hydrangea radiata* 'SMNHRLL'.

PROPAGATION

Time to initiate roots: Approximately 18 days.

Time to produce a rooted young plant: Approximately 60 days.

Propagation method: Softwood cuttings.

Roots: Thick, fine, fibrous, moderately dense. White and brown in color, not accurately measured with R.H.S. chart.

PLANT

Plant type: Flowering deciduous perennial shrub.

Age of plant described: Approximately 2 to 3 years old.

Growth habit: Upright.

Overall plant shape: V-Shaped.

Height: 64 cm.

Plant spread: 86 cm.

Growth rate: Good.

Plant vigor: Moderate.

Branching habit: Abundant upright branches at acute angles from center.

Length of primary lateral branches: Average 42 cm.

Diameter of lateral branches: 5 mm.

Quantity of lateral branches: About 100.

Stem:

- *Stem shape*.—Round.
- *Stem strength*.—Strong.
- *Color*.—Immature: RHS Brown N200C with Greyed-Purple 187A. Mature: RHS Brown 200C.
- *Texture*.—Pubescent new growth.
- *Aspect*.—Straight, occurring at 15° to 90° from center.

Internode length: Average 5.0 cm.

FOLIAGE

Leaf:

- *Arrangement*.—Opposite.
- *Leaf shape*.—Ovate.
- *Average length*.—5.5 to 8 cm.
- *Average width*.—3 to 4 cm.
- *Apex*.—Cuspidate.
- *Base*.—Obtuse.
- *Margin*.—Serrate.
- *Texture of top surface*.—Leathery, pubescent.
- *Texture of bottom surface*.—Leathery, pubescent.
- *Color*.—Young foliage upper side: RHS Green 137A. Young foliage under side: RHS Grey-Green 191A. Mature foliage upper side: RHS Green 137A. Mature foliage under side: RHS Grey-Green 191A.
- *Venation*.—Pattern: Pinnate. Color upper side: RHS Greyed-Yellow 162C. Color under side: RHS Grey-Green 195C.
- *Petiole*.—Average Length: Average range 2 to 4.5 cm. Diameter: 1 mm. Petiole color upper side: RHS Greyed-Brown N199B. Petiole color lower side: RHS Greyed-Green 194A. Petiole Texture upper side: Pubescent. Petiole Texture lower side: Pubescent.

FLOWER

Natural flowering season: Summer.

Inflorescence:

- *Type*.—Lacecap umbel.
- *Quantity of flowers per inflorescence*.—Fertile flowers: 200-300. Sterile flowers: about 10.
- *Shape*.—Flattened disc.
- *Height*.—1 cm.
- *Diameter*.—10 cm.
- *Fragrance*.—Slightly earthy scent.

Sterile flower:

- *Bud shape*.—Round.
- *Bud length*.—2 mm.
- *Bud diameter*.—2 mm.
- *Bud color*.—RHS Greyed-Purple 185C.
- *Aspect*.—Upright and pendulous.
- *Flower depth*.—About 8 mm.
- *Flower diameter*.—About 2.0 cm.
- *Persistence*.—Self-cleaning.
- *Sterile flower petals*.—Petals do not develop/open, or not present.

Sterile flower sepal:

- *Arrangement*.—Cruciform, rotate or trifoliate.
- *Number*.—3 or 4.
- *Shape*.—Wide elliptical.
- *Tip*.—Acute.
- *Base*.—Obtuse.
- *Margin*.—Entire.
- *Length*.—1 cm.
- *Width*.—1 cm.
- *Texture, upper*.—Smooth.
- *Texture, lower*.—Smooth.
- *Color*.—Upper surface at first opening: White 155A flushed greyed-purple 185C. Under surface at first opening: White 155A with some greyed-purple 185C near the edges. Upper surface at maturity: White 155A flushed greyed-purple 185C. Flushing stronger near the margins. Under surface at maturity: White 155A with some greyed-purple 185C.

Sterile flower pedicel:

*Length.*—1.0 cm.

*Diameter.*—1.0 mm.

*Angle.*—45°.

*Strength.*—Flexible.

*Texture.*—Slightly pubescent.

*Color.*—Near Green 142C with some Greyed-Purple 185C.

Fertile flower:

*Bud shape.*—Sphere.

*Bud length.*—1 mm.

*Bud diameter.*—1 mm.

*Bud color.*—Near Greyed-Purple 185B.

*Flower aspect.*—Upright.

*Flower shape.*—Rotate.

*Flower diameter.*—5 mm.

*Flower length.*—5 mm.

*Flower depth.*—2 mm.

*Persistence.*—Self-cleaning.

Fertile flower petals:

*Arrangement.*—Rotate.

*Quantity.*—5.

*Length of petal.*—2 mm.

*Width of petal.*—1 mm.

*Apex.*—Acute.

*Shape of petal.*—Elliptic.

*Petal margin.*—Entire.

*Petal base.*—Truncate.

*Petal texture.*—Smooth, upper and under side.

*Color.*—Upper surface at first opening: Near Greyed-Purple 185D. Under surface at first opening: Near Greyed-Purple 185D. Upper surface at maturity: Near Greyed-Purple 185D. Under surface at maturity: Near Greyed-Purple 185D.

Fertile flower sepal: Inconspicuous, less than 0.5 mm.

Fertile flower pedicel:

*Angle.*—0° to 45°.

*Strength.*—Flexible.

*Length.*—1 cm.

*Width.*—1 mm.

*Texture.*—Slightly pubescent.

*Color.*—Near RHS Green 142D.

REPRODUCTIVE ORGANS

Sterile flowers: None.

Fertile flowers:

Stamens:

*Number.*—About 10.

*Filament length.*—5 mm.

*Filament color.*—RHS White NN155A.

Anthers:

*Shape.*—Globular.

*Length.*—1 mm.

*Color.*—RHS Greyed-White 156A.

*Pollen color.*—RHS White N155A.

*Pollen amount.*—Moderate.

Pistil:

*Number.*—2.

*Length.*—1 mm.

*Style.*—Length: 0.8 mm. Color: White N155A.

*Ovary color.*—White N155A.

*Stigma.*—Shape: Bi-lobed. Color: White N155A

OTHER CHARACTERISTICS

Seeds and fruits: None observed.

Disease/pest resistance: Neither resistance nor susceptibility to normal diseases and pests of *Hydrangea* have been observed.

Temperature tolerance: Tolerates temperatures in USDA Zones 3 to 9.

What is claimed is:

1. A new and distinct cultivar of *Hydrangea* plant named 'SMNHRLL' as herein illustrated and described.

* * * * *